United States Patent [19]
Raeymaekers et al.

[11] Patent Number: 5,256,681
[45] Date of Patent: Oct. 26, 1993

[54] [5(6)-(BENZISOXA-,BENZISOTHIA-OR INDAZOL-3-YL)-1H-BENZIMIDAZOL-2-YL]CARBAMATES

[75] Inventors: Alfons H. M. Raeymaekers, Beerse; Eddy J. E. Freyne, Rumst; Gustaaf M. Boeckx, Oud-Turnhout, all of Belgium

[73] Assignee: Janssen Pharmaceutica N.V., Beerse, Belgium

[21] Appl. No.: 752,521

[22] PCT Filed: Mar. 15, 1989

[86] PCT No.: PCT/EP90/00373
§ 371 Date: Aug. 27, 1991
§ 102(e) Date: Aug. 27, 1991

[87] PCT Pub. No.: WO90/10630
PCT Pub. Date: Sep. 20, 1990

[51] Int. Cl.$^5$ .............. C07D 413/04; C07D 403/04; C07D 417/04; A61K 31/415

[52] U.S. Cl. .............. 514/373; 514/379; 514/388; 548/212; 548/241; 548/305.1

[58] Field of Search .............. 548/212, 241, 305.1; 514/373, 379, 388

[56] References Cited

U.S. PATENT DOCUMENTS 3,657,267  4/1972  Van Gelder .............. 548/212

*Primary Examiner*—Robert Gerstl
*Attorney, Agent, or Firm*—Charles J. Metz

[57] ABSTRACT

[5(6)-(benzisoxa-, benzisothia- or indazol-3-yl)-1H-benzimidazol-2-yl]carbamates of formula (I) wherein $R^1$ is hydrogen, $C_{1-4}$alkyl, halo, hydroxy or $C_{1-4}$alkyloxy; $R^2$ is $C_{1-4}$alkyl; and X is O, S, SO, $SO_2$ or $NR^3$, said $R^3$ being hydrogen, $C_{1-4}$alkyl, aryl or aryl$C_{1-4}$alkyl. The compounds of formula (I) have anthelminthic properties. Compositions containing said compounds as active ingredient, a method of combating helminths, and a process for preparing said compounds and compositions.

7 Claims, No Drawings

[5(6)-(BENZISOXA-,BENZISOTHIA-OR INDAZOL-3-YL)-1H-BENZIMIDAZOL-2-YL]CARBAMATES

BACKGROUND OF THE INVENTION

A large number of benzimidazole carbamates have been described as anthelminths. As most successful representatives there may be named mebendazole and flubendazole both described in U.S. Pat. No. 3,657,267, albendazole described in U.S. Pat. No. 3,915,986, oxibendazole described in U.S. Pat. No. 3,682,952 and fenbendazole described in U.S. Pat. No. 3,954,791.

The benzimidazole carbamates of the present invention differ therefrom by the fact that they contain a benzimidazole moiety which is invariably substituted in the 5(6) position with a benzisoxa-, benzisothia-, or indazol radical and in particular by their favourable anthelminthic spectrum.

DESCRIPTION OF THE INVENTION

The present invention is concerned with novel benzimidazole carbamates of formula

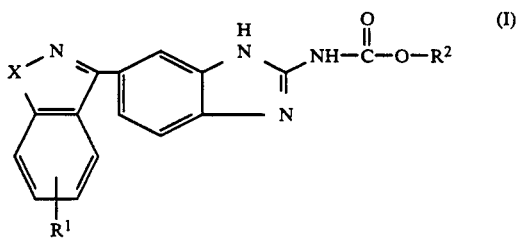

the acid addition or metal substitution salts thereof and the stereochemically isomeric forms thereof, wherein $R^1$ is hydrogen, $C_{1-4}$alkyl, halo, hydroxy or $C_{1-4}$alkyloxy;

$R^2$ is $C_{1-4}$alkyl; and

X is O, S, SO, $SO_2$ or $NR^3$, said $R^3$ being hydrogen, $C_{1-4}$alkyl, aryl or aryl$C_{1-4}$alkyl;

wherein aryl is phenyl optionally substituted with 1 or 2 substitutents each independently selected from $C_{1-4}$alkyl, halo, hydroxy or $C_{1-4}$alkoxy.

As used in the foregoing definitions the term halo is generic to fluoro, chloro, bromo and iodo and the term "$C_{1-4}$alkyl" is meant to include straight and branch chained saturated hydrocarbon radicals having from 1 to 4 carbon atoms such as, for example, methyl, ethyl, propyl, 1-methylethyl, 1,1-dimethylethyl, 2-methylpropyl, butyl and the like.

The compounds of formula (I) may occur in tautomeric forms which tautomeric forms are intended to be within the scope of the present invention.

Preferred compounds within the present invention are those compounds of formula (I) wherein $R^1$ is hydrogen or halo; $R^2$ is $C_{1-4}$alkyl; and X is O,S or $NR^3$, said $R^3$ being hydrogen, $C_{1-4}$alkyl or aryl.

Particularly preferred compounds within the present invention are those preferred compounds wherein $R^1$ is hydrogen or fluoro and/or $R^2$ is methyl or ethyl and/or X is O,S or $NR^3$, wherein $R^3$ is hydrogen, methyl or phenyl.

More preferred compounds within the invention are those preferred compounds wherein $R^1$ is hydrogen, $R^2$ is methyl and X is O or S.

The most preferred compounds of the invention are selected from the group consisting of methyl [5-(1,2-benzisoxazol-3-yl)-1H-benzimidazol-2-yl]carbamate and the pharmaceutically acceptable acid addition or metal substitution salts thereof.

The acid addition and metal substitution salts as mentioned hereinabove comprise the therapeutically active, and in particular, pharmaceutically acceptable non-toxic acid addition and metal substitution salt forms which the compounds of formula (I) are able to form. The acid addition salts can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The metal substitution salts hereinabove are meant to comprise the therapeutically active non-toxic metal substitution salt forms or metal complexes which the compounds of formula (I) are able to form, the term metal also comprising ammonium. The latter can conveniently be obtained by treating the compounds of formula (I) with appropriate inorganic bases or salts, for example, ammonia or bases derived from alkali or earth alkaline metals, e.g. alkali metal or earth alkaline metal oxides or hydroxides such as sodium hydroxide, calcium hydroxide, calcium oxide and the like. Conversely the salt form can be converted by treatment with alkali into the free base form or with acid into the free acidic form. The term salt also comprises the hydrates and solvent addition forms which the compounds of formula (I) are able to form. Examples of such forms are e.g. hydrates, alcoholates and the like.

The compounds of formula (I) can generally be prepared by ring closure of an appropriately substituted benzenediamine of formula (II) or an acid addition salt thereof, with an appropriate isourea or isothiourea derivative of formula (III).

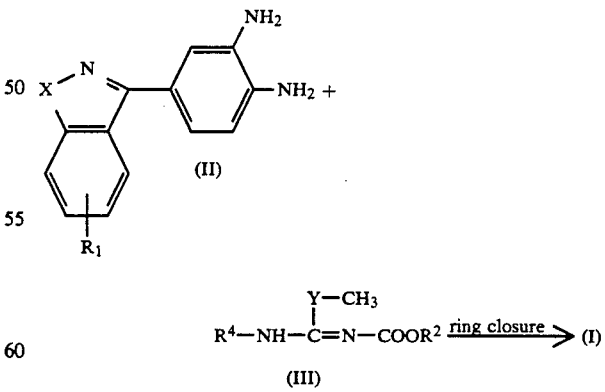

In the formulae (II) and (III) the symbols X, $R^1$ and $R^2$ have the same meaning as described for formula (I) hereinbefore, whereas Y is S or O and $R^4$ is hydrogen or a radical of formula $-COOR^2$.

Without being bound by any theory, it is assumed that the intermediates of formula (III) may occur in tautomeric forms as tentatively illustrated in the following scheme.

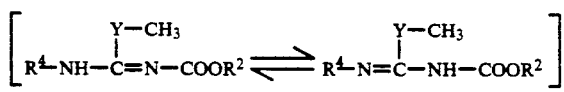

Such tautomeric forms are naturally intended to be within the meaning of formula (III).

The cyclization of (II) with (III) can conveniently be carried out by stirring the reactants in a suitable solvent preferably in the presence of an appropriate acid, either organic or inorganic. Organic acids comprise, for example, carboxylic acids, e.g. formic, acetic or propionic acid. Somewhat elevated temperatures may be appropriate to enhance the rate of the reaction and most preferably the reaction is carried out at the reflux temperature of the reaction mixture. In certain instances it may be advantageous to carry out the reaction under pressure. Suitable solvents comprise organic solvents such as, for example, lower alkanols, e.g. methanol, ethanol, 2-propanol and the like alcohols; aromatic hydrocarbons, e.g. benzene, methylbenzene and the like; halogenated hydrocarbons, e.g. trichloromethane, dichloromethane, trichloroethane, trichloroethylene, chlorobenzene and the like; ethers such as tetrahydrofuran; ketones such as 2-propanone, 3-methyl-2-butanone; esters such as ethyl acetate; nitriles, e.g. acetonitrile and the like; and other common polar aprotic solvents such as, N,N-dimethylformamide, N,N-dimethylacetamide and the like solvents. Mixtures of such solvents with water may also be employed, e.g. mixtures of water with lower alkanols.

Benzimidazole carbamates of formula (I) may also be prepared by reacting a benzenediamine of formula (II) or an acid addition salt thereof with a cyanocarbamate of formula (IV).

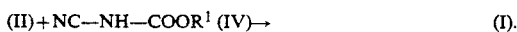

Said reaction may be effected according to art-known procedures as described, for example, in U.S. Pat. Nos. 3,682,952 and 3,969,526, by reacting a benzenediamine of formula (II) or an acid addition or metal substitution salt thereof with a cyanocarbamate of formula (IV) in a suitable solvent such as, for example, water; a lower alkanol, e.g. methanol, ethanol; a ketone, e.g. 2-propanone; a polar aprotic solvent, e.g. N,N-dimethylformamide, N,N-dimethylacetamide, pyridine; or a mixture of such solvents, optionally in the presence of an acid such as, for example, a mineral acid, e.g. hydrochloric acid. Somewhat elevated temperatures may be appropriate to enhance the rate of the reaction, more in particular the reaction may be conducted between 30° and 100° C. In some instances it is appropriate to prepare the cyanocarbamate of formula (IV) in situ by reacting an appropriate halo formate ester (V), e.g. chloroformate ester with an aqueous solution of cyanamide or its calcium salt in the presence of an appropriate base such as, for example, an alkali metal carbonate or hydroxide.

Alternatively, the benzimidazole carbamates of formula (I) may be prepared by reacting a benzenediamine of formula (II) with cyanogen bromide (VI) and reacting the thus obtained 2-aminobenzimidazole (VII) with an appropriate haloformate ester (V), e.g. chloroformate ester.

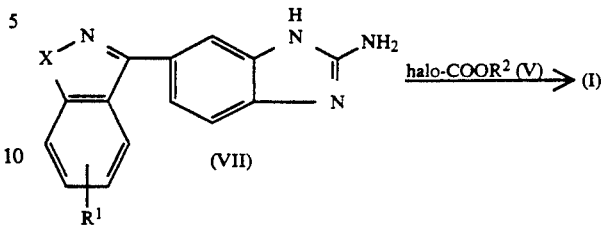

The benzimidazole carbamates of formula (I) may alternatively be prepared under similar procedures as are described in the literature for the preparation of related benzimidazole carbamates starting from appropriately substituted benzenediamines. A number of such procedures are described, for example, in "The chemistry of Heterocyclic Compounds" Vol. 40, part 1, pages 1–60, J. Wiley & Sons, New York (1981) and the references and Patents cited therein.

In all of the foregoing and in the following preparations, the reaction products may be isolated from the reaction mixture and, if necessary, further purified according to methodologies generally known in the art such as, for example, extractions, distillation, crystallization, trituration and chromatography.

The compounds of formula (I) may also be converted into each other following art-known functional group transformation procedures.

The compounds of formula (I), wherein X is S may be converted into the corresponding compounds of formula (I), wherein X is SO or SO₂ by an appropriate oxidation reaction, e.g. by reacting the former compounds with a suitable oxidating agent such as, for example, sodium chlorate, potassium permanganate, potassium periodate, a peroxide, e.g. 3-chlorobenzenecarboperoxoic acid, hydrogen peroxide and the like in a suitable solvent such as, an ether, e.g. tetrahydrofuran, 1,1'-oxybisethane, a hydrocarbon, e.g. benzene, a halogenated hydrocarbon, e.g. dichloromethane and the like. In the instance where a sulfoxide is desired, said oxidation reaction is preferably conducted at lower temperatures with approximately one equivalent of the oxidating agent, while were a sulfonyl is desired, said oxidation reaction may be conducted at room or at an elevated temperature with an excess of oxidating agent.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (II) can be prepared from the corresponding nitro-substituted intermediates (VIII) following art-known nitro-to-amine reduction procedures such as for example, catalytic hydrogenation in a suitable solvent e.g. methanol or ethanol, in the presence of hydrogen and an appropriate catalyst e.g. platinum-on-charcoal, palladium-on-charcoal, Raney nickel, and the like. In some cases it may be useful to add an appropriate catalyst poison such as thiophene to the reaction mixture. Alternatively, said nitro group may also be reduced to an amino group by reaction with a reducing agent such as, for example, sodium sulfide, sodium dithionate and the like. Said reaction can be carried out by stirring the reactants in a suitable solvent such as for example, water, an alcohol e.g. methanol, ethanol or a mixture of such solvents.

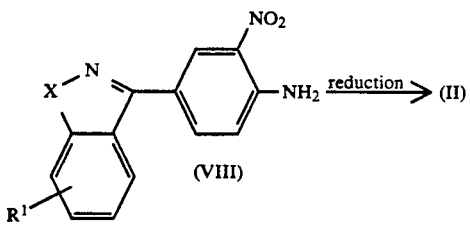

The intermediates of formula (VIII), wherein X is S, said compounds being represented by formula (VIII-a), can be prepared by reacting an appropriately substituted benzoyl of formula (IX) with sulfur and ammonia in a reaction-inert solvent such as, for example, an ether, e.g. 1,1'-oxybismethane, 2-methoxyethanol and the like, optionally under pressure.

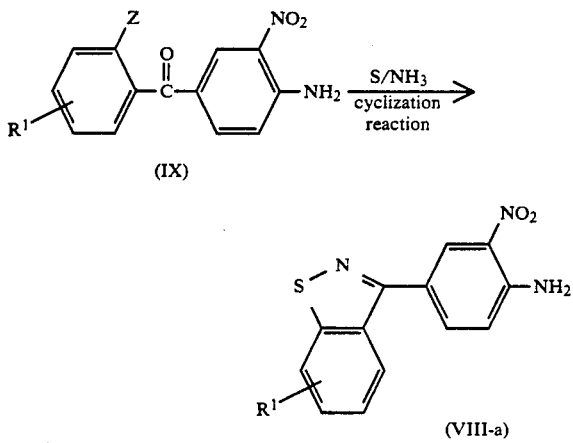

In formula (IX) Z represents an appropriate leaving group, such as, for example, halo, e.g. fluoro or chloro; or a nitro group.

The intermediates of formula (VIII), wherein X is $NR^{3-a}$, with $R^{3-a}$ being hydrogen or $C_{1-4}$alkyl, said intermediates being represented by formula (VIII-b), can be obtained by reacting the benzoyl intermediate (IX) with an appropriate hydrazine derivative $R^{3-a}$—NH—$NH_2$ (X) or an acid addition salt thereof.

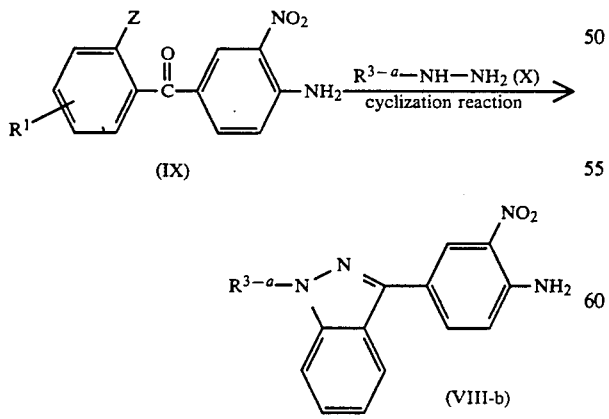

Said reaction can be carried out in a suitable reaction-inert solvent optionally in the presence of a suitable base. Suitable solvents are, for example, water, alkanols, e.g. methanol, ethanol, 1-butanol and the like. Appropriate bases preferably are amines such as N,N-diethylethanamine, 4-ethylmorpholine, pyridine and the like.

The benzoyl intermediates of formula (IX) can also be treated with hydroxylamine or an appropriate hydrazine derivative $R^{3-b}$—NH—$NH_2$ (XI) or an acid addition salt thereof to form an intermediate of formula (XII) wherein X is O or $NR^{3-b}$, said X being represented by $X^1$, with $R^{3-b}$ being aryl or aryl$C_{1-4}$alkyl. Said reaction can be carried out with or without a suitable reaction-inert solvent and optionally in the presence of a base. Suitable solvents are, for example, water, alkanols, e.g. methanol, ethanol, 1-butanol and the like. Appropriate bases preferably are amines, such as N,N-diethylethanamine, 4-ethylmorpholine, pyridine and the like.

The thus prepared intermediates of formula (XII) can readily be cyclized to obtain intermediates of formula (VIII), wherein X is O or $NR^{3-b}$ with $R^{3-b}$ being aryl or aryl$C_{1-4}$alkyl, said intermediates being represented by formula (VIII-c).

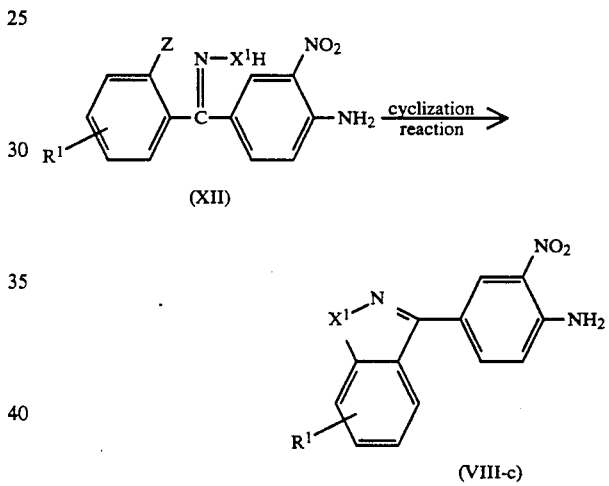

Said cyclization reaction may conveniently be conducted by treatment with an appropriate base, preferably in a suitable reaction-inert solvent such as, for example, water, hydrocarbons, e.g., benzene, dichloromethane and the like; lower alkanols, e.g. methanol, ethanol and the like; dipolar aprotic solvents, e.g. N,N-dimethylformamide, N,N-dimethylacetamide, dimethyl sulfoxide and the like; or mixtures of said solvents. Appropriate bases are for example, hydroxides, alkoxides or hydrides, e.g. sodium hydroxide, sodium methoxide, sodium hydride and the like bases.

The intermediates of formula (IX) can be obtained by an aromatic nucleophilic substitution reaction of the halo group of intermediate (XIII).

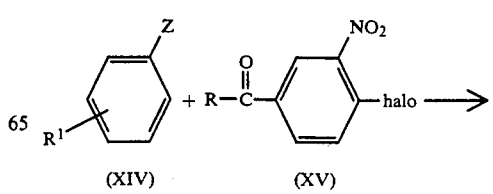

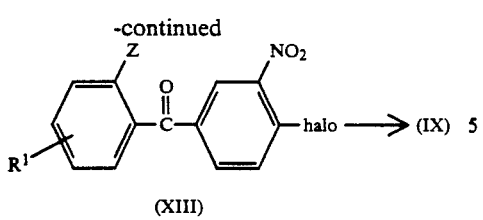

(XIII)

In the foregoing definitions the term halo is generic to fluoro, chloro, bromo and iodo. The nucleophilic substitution reaction can be carried out with ammonia in a reaction-inert solvent such as for example, a hydrocarbon, e.g. pentane, benzene; a halogenated hydrocarbon such as dichloromethane and the like; an alcohol, e.g. methanol, ethanol and the like; a dipolar aprotic solvent, e.g. N,N-dimethylformamide, N,N-dimethylacetamide, dimethyl sulfoxide and the like. The intermediates of formula (XIII) can in turn be obtained by Friedel-Crafts acylation of a benzene of formula (XIV) with an acyl halide, a carboxylic acid or an anhydride of formula (XV). Said Friedel-Crafts reaction can be carried out by stirring the reaction mixture optionally in the presence of a reaction-inert solvent and in the presence of a catalyst such as, for example, a Lewis acid, e.g. ferric chloride, ferric bromide, aluminum trichloride and the like. Suitable solvents are, for example, hydrocarbons, e.g. pentane, hexane, nitrobenzene, dichloromethane, tetrachloromethane and the like.

The intermediates of formula (VIII) wherein X is O, said intermediates being represented by formula (VIII-d), may also be prepared by cyclizing an activated oxime derivative of formula (XVI), wherein T is an acyl residue and more particularly is (C$_{1-4}$alkyl or aryl)carbonyl, e.g. propionyl and the like; (C$_{1-4}$alkyl or aryl)oxycarbonyl, e.g. methoxycarbonyl and the like; (C$_{1-4}$alkyl or aryl)sulfonyl, e.g. methanesulfonyl, benzenesulfonyl and the like; N-acylaminocarbonyl, e.g. trichloromethylcarbonylaminocarbonyl and the like.

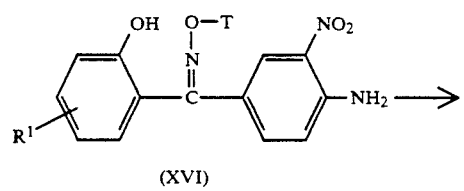

(XVI)

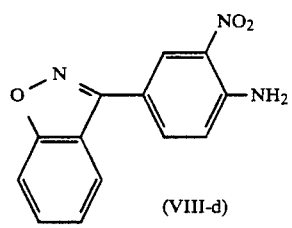

(VIII-d)

Said cyclization reaction of the activated oxime derivative of formula (XVI) may conveniently be conducted by treatment with an appropriate base, preferably in a suitable reaction-inert solvent. In some instances however, it may be advantageous not to add a base to the reaction mixture and to remove the acid liberated during the reaction by distillation. Alternatively, said cyclization may also be effected by heating the oxime derivative (XVI) in vacuo without a solvent. Appropriate bases are for example, alkali and earth alkaline metal carbonates, hydrogen carbonates and amines, e.g. sodium carbonate, potassium carbonate, sodium hydrogen carbonate, N,N-diethylethanamine, pyridine and the like bases. Suitable solvents for said cyclization are, for example, aromatic hydrocarbons, e.g. benzene, methylbenzene and the like; ethers, e.g. 1,1'-oxybisethane, tetrahydrofuran, 1,4-dioxane and the like; dipolar aprotic solvents, e.g. N,N-dimethylformamide, N,N-dimethylacetamide and the like; halogenated hydrocarbons, e.g. trichloromethane, tetrachloromethane and the like solvents.

The intermediates of formula (II), wherein X is NR$^3$ and R$^3$ is hydrogen, C$_{1-4}$alkyl, aryl, or arylC$_{1-4}$alkyl, said intermediates being represented by formula (II-a), may also be prepared by a series of conversions starting from an aniline of formula

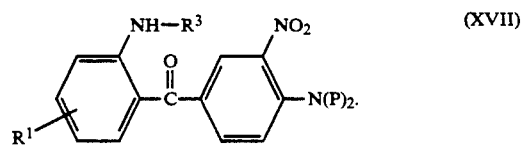

Preferably, the aniline (XVII) is treated with an alkali metal nitrite, e.g. sodium nitrite, in an aqueous acidic medium thus obtaining the corresponding N-nitroso compound (XVIII-a) or, in case R$^3$ is hydrogen, thus obtaining the diazonium salt (XVIII-b).

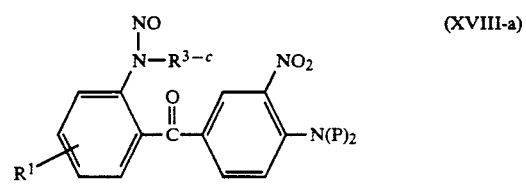

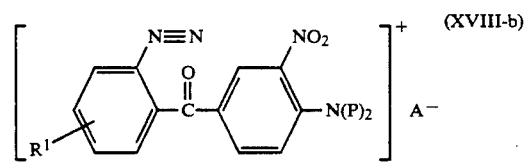

In formula (XVIII-a) R$^{3-c}$ has the same meaning as R$^3$ with the proviso that hydrogen is excluded and in formula (XVIII-b) A-represents the conjugated base of the acid of the aqueous acidic medium mentioned hereinabove. The N-nitroso compound (XVIII-a) or the diazonium salt (XVIII-b) is treated with an appropriate reducing agent such as, for example, hydrogen in the presence of a hydrogenation metal catalyst, e.g. Raney nickel or Raney cobalt; or a sulfite, e.g. sodium sulfite; thus yielding the corresponding hydrazine derivative of formula (XIX), which in most instances spontaneously, or if necessary upon increasing the temperature, will cyclize to a compound of formula (II-a).

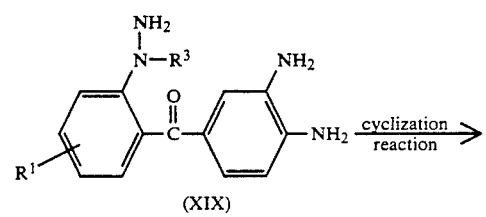

(XIX)

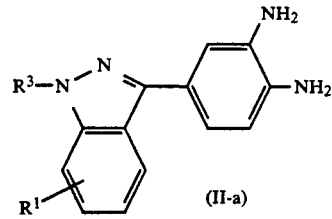

(II-a)

In the formulae (XVII), (XVIII) and (XIX) P represents a suitable protective group which preferably is readily removable by hydrogenation such as, phenylmethyl and the like. When using such protective group for the hydrogenation of (XVIII-a) or (XVIII-b), the unprotected intermediate (XIX) is obtained. In other instances, N-protected derivatives of formula (XIX) are obtained which may be deprotected, or may be converted as such to the N-protected intermediate (II-a), which is afterwards deprotected.

The isourea or isothiourea derivatives of formula (III) may be prepared by the reaction of an iso(thio)urea of formula (XX) or an acid addition salt thereof with an appropriate haloformate ester (V), e.g. chloroformate ester, in the presence of a base, as illustrated in the following scheme; with Y and $R^4$ being as defined hereinabove.

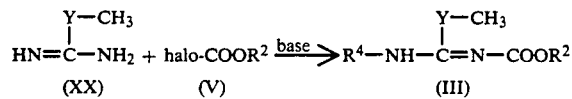

Suitable bases for the purpose of this procedure include metal alkoxides, metal hydroxides, alkali or earth alkali metal carbonates, hydrogen carbonates or organic bases, e.g. sodium methoxide, sodium hydroxide, sodium carbonate, sodium hydrogen carbonate, N,N-diethylethanamine and the like.

In some instances the compounds of formula (I) and some of the intermediates in this invention may have an asymmetric carbon atom in their structure, e.g. when $R^2$ is a branched alkyl. This chiral center may be present in a R- and a S-configuration, this R- and S-notation being in correspondence with the rules described in J. Org. Chem., 35, 2849–2867 (1970). These stereochemically isomeric forms of the compounds of formula (I) are naturally intended to be embraced within the scope of the invention.

Pure stereochemically isomeric forms of the compounds of this invention may be obtained by the application of art known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids, or the like methods.

Pure stereochemically isomeric forms may also be derived from the corresponding pure stereochemically isomeric forms of the appropriate starting materials, provided that the reaction occurs stereospecifically.

The compounds of formula (I), the pharmaceutically acceptable acid-addition salts and stereochemically isomeric forms thereof have anthelminthic properties, in particular they posses a broad spectrum activity against parasites of warm blooded animals (human or animal), including both mature and immature parasitic forms, as represented for example by Nematodes, such as, *Syngamus trachea* in turkeys and pheasants, Ascaridia and Heterakis in chickens, *Toxocara cati* in cats, *Ankylostoma tubaeforme* in cats, *Toxocara canis* in dogs, *Toxascaris leonina* in dogs, *Uncinaria stenocephala* in dogs, *Ankylostoma caninum* in dogs, *Trichuris vulpis* in dogs, *Trichinella spiralis* in pigs and rats, *Haemonchus contortus* in sheep, *Dictyocaulus filaria* in sheep and Trichostrongylides in sheep. Some compounds of the present invention are even found to be active against Cestodes, such as, *Taenia pisiformis* in dogs, *Taenia hydatigena* in dogs, *Taenia ovis* in dogs, *Dipylidium caninum* in dogs, *Taenia taeniaeformis* in cats, Moniezia in sheep, Anitellina sp in sheep, Raillietina, *Hydatigera taeniaformis* and the like. In particular, the compounds of the invention are found to exhibit high activity against various helminths infecting the intestinal tract of man and economically important animals, such as, sheep, cattle, horses, pigs and poultry, coupled with low systemic toxicity to the host.

The anthelminthic properties of compounds of formula (I) can be demonstrated for example in the "*Taenia pisiformis* in artificially infected dogs"-test and the "*Heterakis gallinarium* in chicken"-test illustrating the useful anthelminthic properties of the compounds of the present invention.

In view of their useful anthelminthic properties the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as a pour-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In the instance where economically important animals are raised in large numbers, particularly poultry and birds, it is advantageous to add the compounds of formula (I) directly to the feed, as such or in the form of a premix or concentrate. In addition, the compounds of formula (I) may also be administered dissolved or suspended in drinking water.

In view of the anthelminthic properties of the compounds of formula (I) it is evident that the present invention provides anthelminthic compositions comprising an anthelminthically effective amount of an active compound of formula (I), either alone or in admixture with other active therapeutic ingredients such as, closantel, in admixture with suitable carriers.

In view of their potent activity in combating helminths the compounds of this invention constitute useful tools for the destroying or prevention of the growth of helminths and more particularly they can effectively be used in the treatment of subjects suffering from such helminths. Therefore the present invention provides a method of destroying or preventing the growth of helminths in warm blooded animals suffering from such helminths by administration of an anthelminthically effective amount of a compound of formula (I), a pharmaceutically acceptable acid addition salt or a possible stereochemically isomeric form thereof.

Those of skill in treating warm blooded animals suffering from such parasites could easily determine the effective amount from the test results presented herein. In general it is contemplated that an effective amount would be from 1 to 100 mg/kg body weight, more particularly between 2.5 and 25 mg/kg body weight, preferably in a single administration.

The following examples are intended to illustrate and not to limit the scope of the present invention. Unless otherwise stated all parts therein by weight.

EXPERIMENTAL PART

A. Preparation of the intermediates

EXAMPLE 1 a) To a stirred mixture of 465 parts of 1,3-difluorobenzene and 133.3 parts of aluminum trichloride was added dropwise a mixture of 110.1 parts of 4-chloro-3-nitrobenzoyl chloride and 116 parts of aluminum trichloride at 70° C. After stirring for 2 hours at reflux temperature, the reaction mixture was poured into ice-water. There were added 127 parts of hydrochloric acid and the product was extracted with trichloromethane. The extract was dried, filtered and evaporated. The residue was stirred in 2,2'-oxybispropane. The product was filtered off and dried, yielding 130 parts (87.4%) of (4-chloro-3-nitrophenyl) (2,4-difluorophenyl)methanone; mp. 90.5° C.(interm. 1).

b) A mixture of 30 parts of intermediate 1 and 165 parts of dimethyl sulfoxide was stirred for 4 hours at room temperature and for 2 hours at 50° C. while ammonia was bubbled through. The reaction mixture was poured into 600 parts of ice-water. The precipitate was filtered off and crystallized from acetic acid. The product was filtered off, washed with 2,2'-oxybispropane and dried, yielding 23.3 parts (83.7%) of (4-amino-3-nitrophenyl) (2,4-difluorophenyl)methanone (interm. 2).

c) A mixture of 23.3 parts of intermediate 2, 29.2 parts of hydroxylamine monohydrochloride and 196 parts of pyridine was stirred for 2 hours at reflux temperature. The reaction mixture was evaporated and the residue was stirred in 250 ml HCl 5%. The product was extracted with a mixture of trichloromethane and methanol (9:1) The extract was dried, filtered and evaporated, yielding 24 parts (97.4%) of (E+Z) (4-amino-3-nitrophenyl) (2,4-difluorophenyl) methanone, oxime (interm. 3).

d) To a stirred mixture of 3.12 parts of a dispersion of sodium hydride in mineral oil (50%) and 47 parts of N,N-dimethylformamide was added dropwise a mixture of 24 parts of intermediate 3 and 94 parts of N,N-dimethylformamide at 25° C. (cooling on ice). The whole was stirred for 1 hour at room temperature and was then poured into ice-water. After acidifying with hydrochloric acid, the solid was filtered off, washed with water and stirred in acetonitrile. The product was filtered off, washed with 2,2'-oxybispropane and dried, yielding 17.7 parts (79.0%) of 4-(6-fluoro-1,2-benzisoxazol-3-yl)-2-nitrobenzenamine; mp. 238.9° C. (interm. 4). In a similar manner there were also prepared: 4-(1,2-benzisoxazol-3-yl)-2-nitrobenzenamine (interm. 5) and 2-nitro-4-(1-phenyl-1H-indazol-3-yl)benzenamine (interm. 6).

EXAMPLE 2

A mixture of 10.4 parts of (4-amino-3-nitrophenyl) (2-fluorophenyl)methanone, 14.03 parts of methylhydrazine and 79 parts of ethanol was stirred for 40 hours at reflux temperature. After cooling, the precipitated product was filtered off, washed with 2,2'-oxybispropane and dried, yielding 5.5 parts (51.3%) of 4-(1-methyl-1H-indazol-3-yl)-2-nitrobenzenamine; mp. 230.6° C. (interm. 7). In a similar manner there was also prepared: 4-(1H-indazol-3-yl)-2-nitrobenzenamine (interm. 8).

EXAMPLE 3

A mixture of 10.4 parts of (4-amino-3-nitrophenyl) (2-fluorophenyl)methanone, 1.3 parts of sulfur, 40 parts of ammonia and 194 parts of 2-methoxyethanol was stirred for 20 hours in an autoclave at 160° C. The reaction mixture was evaporated and the residue was stirred in dichloromethane. The product was filtered off and dried, yielding 3.1 parts (28.6%) of 4-(1,2-benzisothiazol-3-yl)-2-nitrobenzenamine (interm. 9).

EXAMPLE 4

A mixture of 7.65 parts of intermediate 5, 24.1 parts of sodium dithionate, 158 parts of ethanol and 100 parts of water was stirred for 2 hours at room temperature and for 1¼ hours at reflux temperature. The solvent was evaporated and to the residue there were added water and sodium carbonate. The product was extracted with a mixture of trichloromethane and methanol (90:10).

The extract was dried, filtered and evaporated, yielding 4.6 parts (68.1%) of 4-(1,2-benzisoxazol-3-yl)-1,2-benzenediamine (interm. 10).

In a similar manner there were also prepared: 4-(6-fluoro-1,2-benzisoxazol-3-yl)-1,2-benzenediamine (interm. 11) and 4-(1,2-benzisothiazol-3-yl)-1,2-benzenediamine (interm. 12).

EXAMPLE 5

A mixture of 4 parts of intermediate 6, 2 parts of a solution of thiophene in methanol 4%, 119 parts of methanol and 89 parts of tetrahydrofuran was hydrogenated at 50° C. and normal pressure with 2 parts of palladium-on-charcoal catalyst 10%. After the calculated amount of hydrogen was taken up, the catalyst was filtered off and the filtrate was evaporated. The residue was co-evaporated with methylbenzene, yielding 3.6 parts (99.9%) of 4-(1-phenyl-1H-indazol-3-yl)-1,2-benzenediamine (interm. 13). In a similar manner there were also prepared: 4-(1-methyl-1H-indazol-3-yl)-1,2-benzenediamine (interm. 14) and 4-(1H-indazol-3-yl)-1,2-benzenediamine (interm. 15).

B. Preparation of the final compounds

EXAMPLE 6

A mixture of 4.5 parts of intermediate 10, 6 parts of methyl ($\alpha$-imino-$\alpha$-methoxymethyl)-carbamate, 4.4 parts of acetic acid and 298 parts of trichloromethane was stirred and refluxed for 30 hours. The precipitated product was filtered off, washed successively with methanol, water, methanol and 2,2'-oxybispropane and dried, yielding 4.5 parts (73.0%) of methyl [5-(1,2-benzisoxazol-3-yl)-1H-benzimidazol-2-yl]-carbamate; mp. >300° C. (compound 1).

In a similar manner there were also prepared the compounds listed in Table 1.

tion and washing in tapewater the eggs were collected by passing the proglottids suspension through a sieve with aperture of 53 micron. The number of eggs was counted and about 1000 eggs were administered by gavage to young rabbits.

After 5 weeks the rabbits had infectious *Cysticercus pisiformis* in the peritoneal cavity. After autopsy of the rabbits the cysticerci were collected and administered orally in a gelatine capsule to young Beagle dogs. The infective dose was about 15 cysticerci.

Two months after the artificial infection the dogs were moved to isolated cages on wire floor to confirm the tapeworms infection by faecal examination.

After a single treatment of these dogs with a compound of formula (I) the faecal material was collected every day for 4 days. Elimination of proglottids and scolices was recorded. Seven days after oral administration of a compound of formula (I) the dogs were autopsied and the efficacy of the compound was determined on the basis of the presence (or absence) of scolices in the intestine. For example, compound No. 1 showed 100% activity after a single treatment with 2.5 mg/kg.

EXAMPLE 8

*Heterakis gallinarum* in chickens

A hybrid line of 4 weeks old male Hisex chickens were infected orally with 600 Heterakis gallinae eggs. The eggs were admixed in the normal chicken feed and administered for two consecutive days.

Five weeks after infection they were treated orally with the test compound in a gelatin capsule at various dose levels. Each day after treatment and for 5 consecutive days the expelled nematodes were counted in the faeces. At the end of the experiment the animals were autopsied. The remaining nematodes were counted and identified. The percent efficacy is calculated, based on

TABLE 1

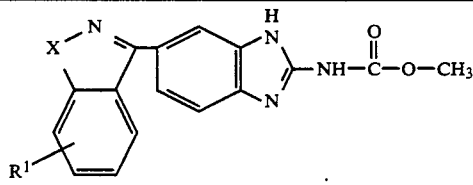

| Comp. No. | X | R$^1$ | mp. (°C.) | Elementary analysis data (carbon, hydrogen, nitrogen) | | | | | | | | |
|---|---|---|---|---|---|---|---|---|---|---|---|---|
| | | | | C | | | H | | | N | | |
| | | | | Theor. value | Exp. value | Diff. | Theor. value | Exp. value | Diff. | Theor. value | Exp. value | Diff. |
| 1 | O | H | >300 | 62.34 | 62.19 | −0.15 | 3.92 | 3.84 | −0.08 | 18.17 | 18.25 | +0.08 |
| 2 | O | 6-F | >300 | 58.9 | 58.55 | −0.35 | 3.40 | 3.32 | −0.08 | 17.17 | 17.30 | +0.13 |
| 3 | N—CH$_3$ | H | 289.6 | 63.54 | 63.00 | −0.54 | 4.71 | 4.62 | −0.09 | 21.79 | 21.57 | −0.22 |
| 4 | N—H | H | 267.5 | 62.54 | 61.65 | −0.89 | 4.26 | 4.20 | −0.06 | 22.79 | 22.35 | −0.44 |
| 5 | S | H | >300 | 59.25 | 58.22 | −1.03 | 3.73 | 3.56 | −0.17 | 17.27 | 16.91 | −0.36 |
| 6 | N—C$_6$H$_5$ | H | decomp. | 68.92 | 67.57 | −1.35 | 4.47 | 4.34 | −0.13 | 18.27 | 17.91 | −0.36 |

C. Biological Examples

The strong anthelminthic activity of the compounds of formula (I) is clearly evidenced by the data obtained in the following experiments, which data are only given to illustrate the useful anthelminthic properties of all the compounds of formula (I) and not to limit the invention either with respect to the scope of susceptible parasites nor with respect to the scope of formula (I).

EXAMPLE 7

*Taenia pisiformis* in artificially infected dogs

Proglottids of *Taenia pisiformis* were collected from the faecal material of the infected dogs. After macerathe ratio:

$$\frac{\text{number of expelled parasites} \times 100}{\text{number of expelled parasites} + \text{number of parasites at autopsy}}$$

For example, compound nos. 3 and 4 showed 100% after a single treatment 10 mg/kg.

D) Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 9

Oral Drops 500 g of the A.I. was dissolved in 0.5 l of 2-hydroxypropanoic acid and 1.5 l of the polyethylene glycol at 60°≈80° C. After cooling to 30°≈40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. (per ml). The resulting solution was filled into suitable containers.

EXAMPLE 10

Oral Solution 9 g of methyl 4-hydroxybenzoate and 1 part of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propanetriol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the A.I. per teaspoonful (5 ml). The resulting solution was filled in suitable containers.

EXAMPLE 11

Capsules 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of the A.I.

EXAMPLE 12

Film-Coated Tablets

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated. The tablet cores were coated with the thus obtained mixture in a coating apparatus.

EXAMPLE 13

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

EXAMPLE 14

Suppositories 3 g A.I. was dissolved in a solution of 3 g 2,3-dihydroxybutanedioic acid in 25 ml polyethylene glycol 400. 12 g surfactant (SPAN ®) and triglycerides (Witepsol 555 ®) q.s. ad 300 g were molten together. The latter mixture was mixed well with the former solution. The thus obtained mixture was poured into moulds at a temperature of 37°-38° C. to form 100 suppositories each containing 30 mg of the active ingredient.

We claim:

1. A chemical compound of formula

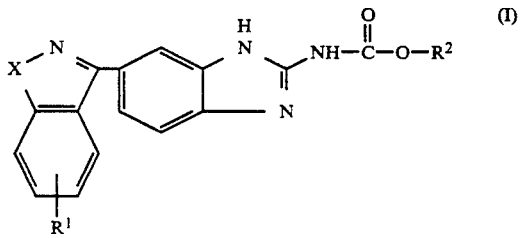

an acid addition or a metal substitution salt thereof, or a stereochemically isomeric form thereof, wherein
  $R^1$ is hydrogen, $C_{1-4}$alkyl, halo, hydroxy or $C_{1-4}$alkyloxy;
  $R^2$ is $C_{1-4}$alkyl; and
  X is O, S, SO, $SO_2$ or $NR^3$, said $R^3$ being hydrogen, $C_{1-4}$alkyl, aryl or aryl$C_{1-4}$alkyl;
  wherein aryl is phenyl optionally substituted with 1 or 2 substituents each independently selected from $C_{1-4}$alkyl, halo, hydroxy or $C_{1-4}$alkoxy.

2. A chemical compound according to claim 1 wherein $R^1$ is hydrogen or halo; $R^2$ is $C_{1-4}$alkyl; and X is O, S or $NR^3$, said $R^3$ being hydrogen, $C_{1-4}$alkyl or aryl.

3. A chemical compound according to claim 2 wherein $R^1$ is hydrogen or fluoro; $R^2$ is methyl or ethyl and X is O, S, $NR^3$, said $R^3$ being hydrogen, methyl or phenyl.

4. A chemical compound according to claim 3 wherein $R^1$ is hydrogen, $R^2$ is methyl and X is O or S.

5. A chemical compound according to claim 1 wherein the compound is methyl [5-(1,2-benzisoxazol-3-yl)-1H-benzimidazol-2-yl]carbamate.

6. An anthelminthic composition comprising a pharmaceutical carrier and as active ingredient an anthelminthic effective amount of at least one compound as claimed in any of claims 1-5.

7. A method of destroying or preventing the growth of helminths in warm-blooded animals suffering from such helminths by the administration of an anthelminthically effective amount of a compound as claimed in any one of claims 1-5.

* * * * *